United States Patent [19]

Danby et al.

[11] Patent Number: 4,846,636

[45] Date of Patent: Jul. 11, 1989

[54] PARENTERAL SOLUTION PUMP ASSEMBLY

[75] Inventors: Hal C. Danby, Sudbury, England; Carl Ritson, San Jose, Calif.

[73] Assignee: Critikon, Inc., Tampa, Fla.

[21] Appl. No.: 168,806

[22] Filed: Mar. 16, 1988

Related U.S. Application Data

[60] Division of Ser. No. 902,616, Sep. 2, 1986, Pat. No. 4,768,547, which is a continuation-in-part of Ser. No. 799,235, Nov. 18, 1985, Pat. No. 4,759,264.

[51] Int. Cl.⁴ .................. F04B 17/00; F04B 35/04
[52] U.S. Cl. .................. 417/413; 417/479; 604/153; 137/454.4; 137/859; 128/DIG. 13
[58] Field of Search ............ 92/89, 91, 96, 98 R, 92/99, 103 SD, 103 R, 103 F, 103 M; 137/454.4, 512, 843, 846, 847, 859; 251/82; 417/395, 413, 479, 305; 128/DIG. 12, DIG. 13; 604/151, 152, 153

[56] References Cited

U.S. PATENT DOCUMENTS

| | | | |
|---|---|---|---|
| 2,497,906 | 2/1950 | Peters et al. | 137/859 X |
| 2,758,609 | 8/1956 | Dickert et al. | 137/659 |
| 4,152,098 | 5/1979 | Moody et al. | 417/413 |
| 4,265,600 | 5/1981 | Mandroian | 417/379 |
| 4,303,376 | 12/1981 | Siekmann | 417/360 |
| 4,305,702 | 12/1981 | Hartley | 417/413 |
| 4,468,222 | 8/1984 | Lundquist | 417/360 X |
| 4,642,098 | 2/1987 | Lundquist | 604/122 |

Primary Examiner—Robert E. Garrett
Assistant Examiner—Mark A. Williamson
Attorney, Agent, or Firm—W. Brinton Yorks, Jr.

[57] ABSTRACT

A disposable diaphragm pump cassette comprises a flexible diaphragm member comprising hinged, rigid plates hingingly mounted on an inflexible plate and opposed to a pumping chamber surface to form a pumping chamber. The pump includes check valve means comprising movable circular plates integrally connected with the inflexible plate by flexible, extendable webs. The flexible diaphragm member comprises at least three inflexible diaphragm plates with edges in a common plane, each diaphragm plate having at least two straight diaphragm plate hinge edges. Each diaphragm plate hinge edge is adjacent to and aligned with a second diaphragm plate hinge edge of an adjacent diaphragm plate. The adjacent edges of each diaphragm plate hinge edge and second diaphragm plate hinge edge are attached together by a flexible hinge strip.

9 Claims, 5 Drawing Sheets

U.S. Patent  Jul. 11, 1989  Sheet 1 of 5  4,846,636
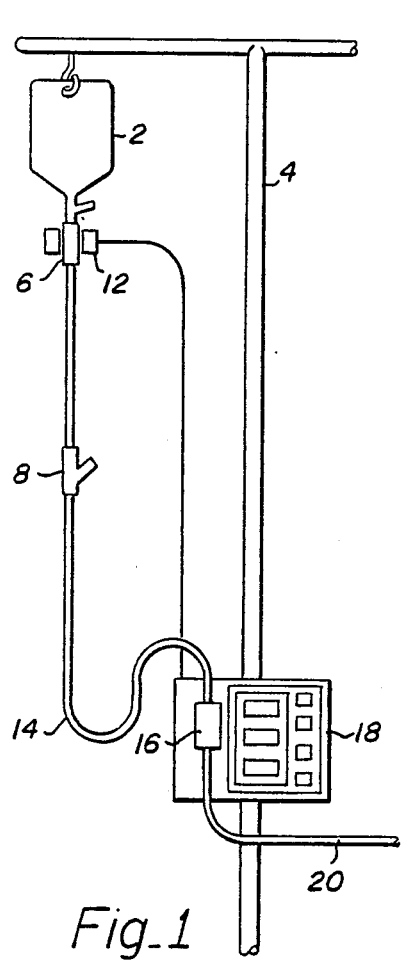
Fig_1
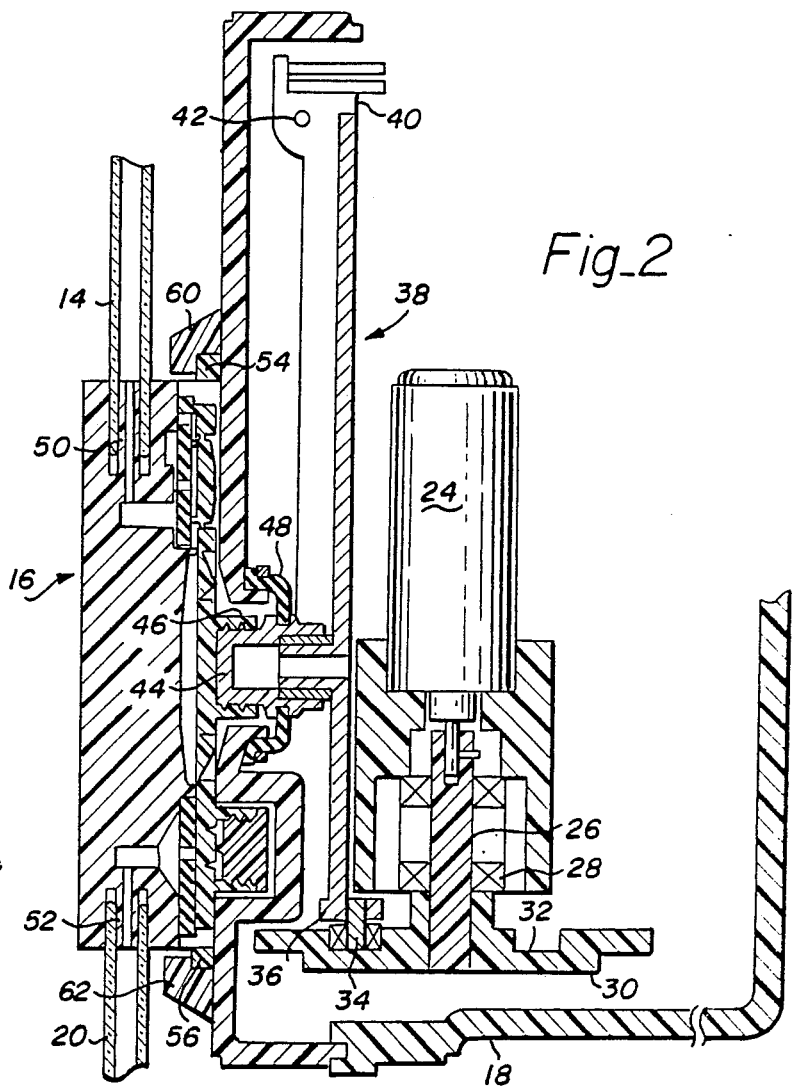
Fig_2

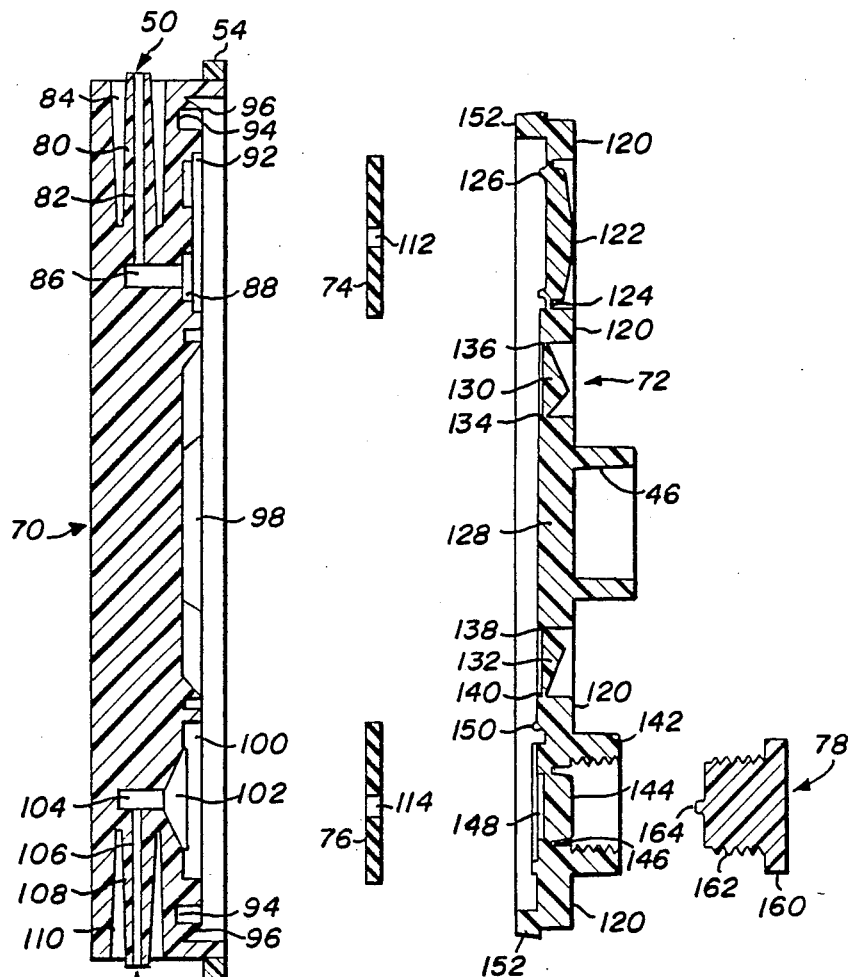
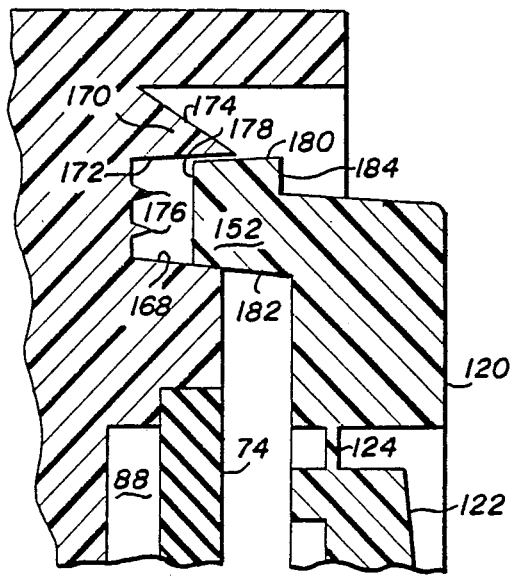
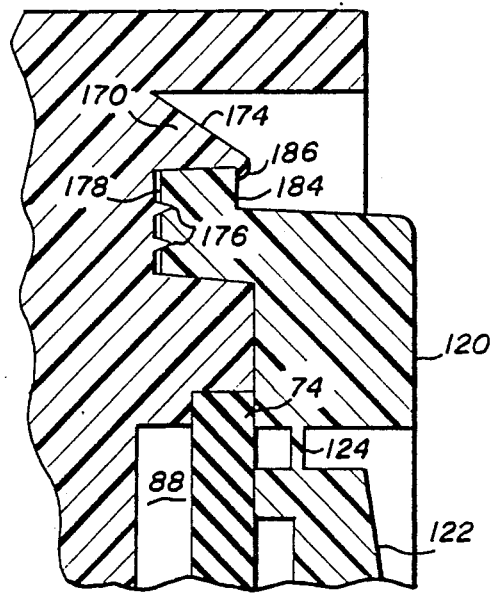
Fig_3
Fig_4
Fig_5

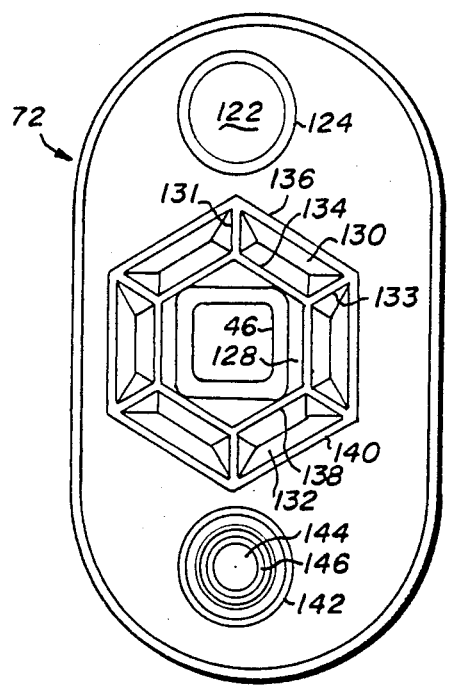
Fig_6
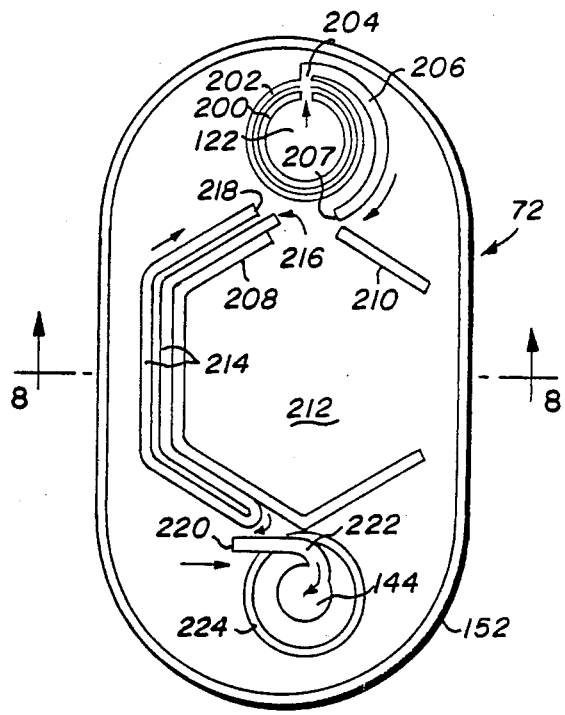
Fig_7
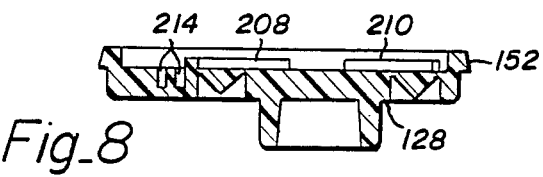
Fig_8
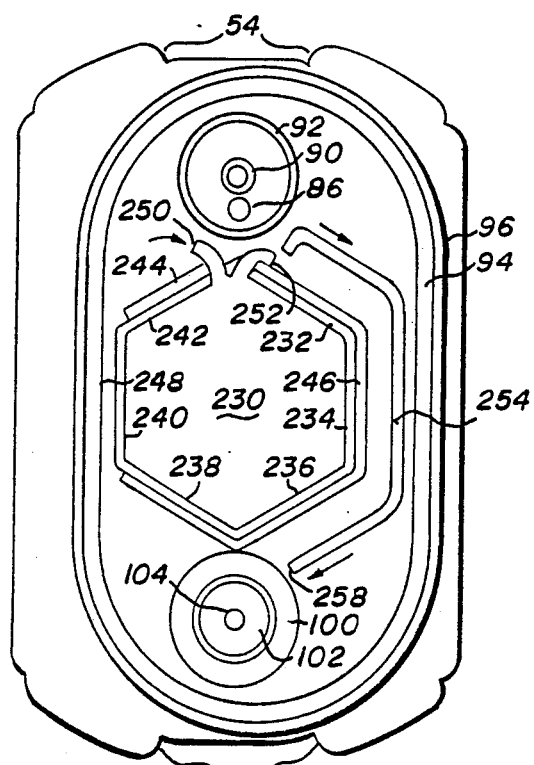
Fig_9
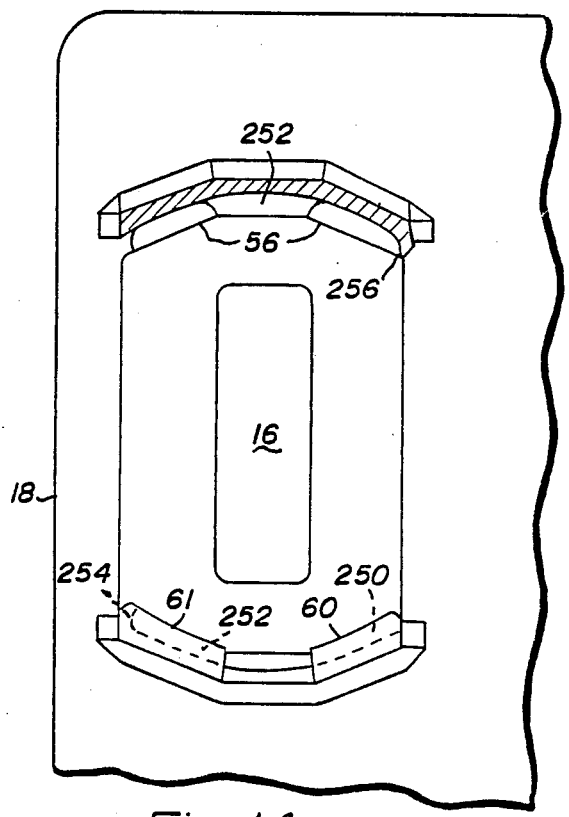
Fig_14

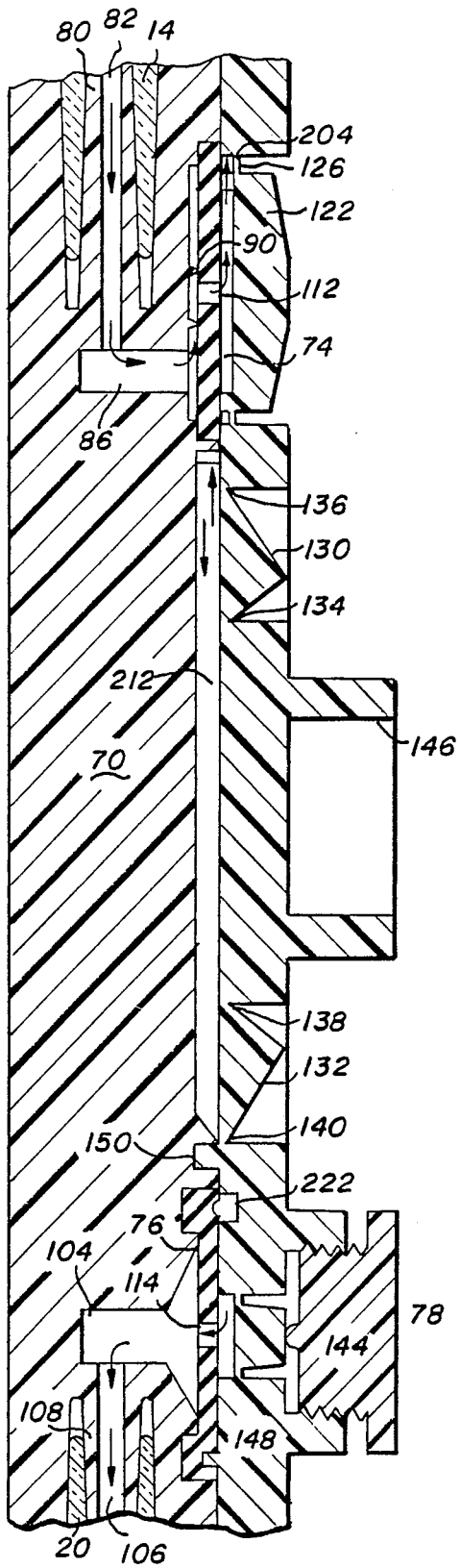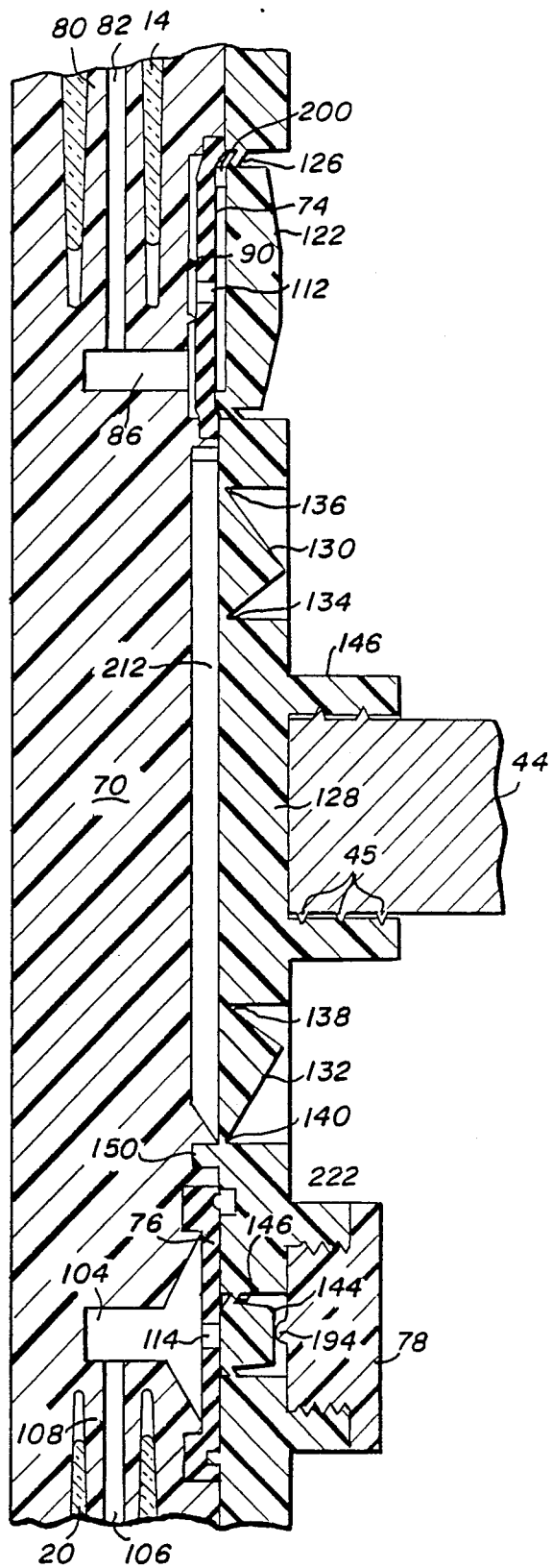
Fig_10   Fig_11

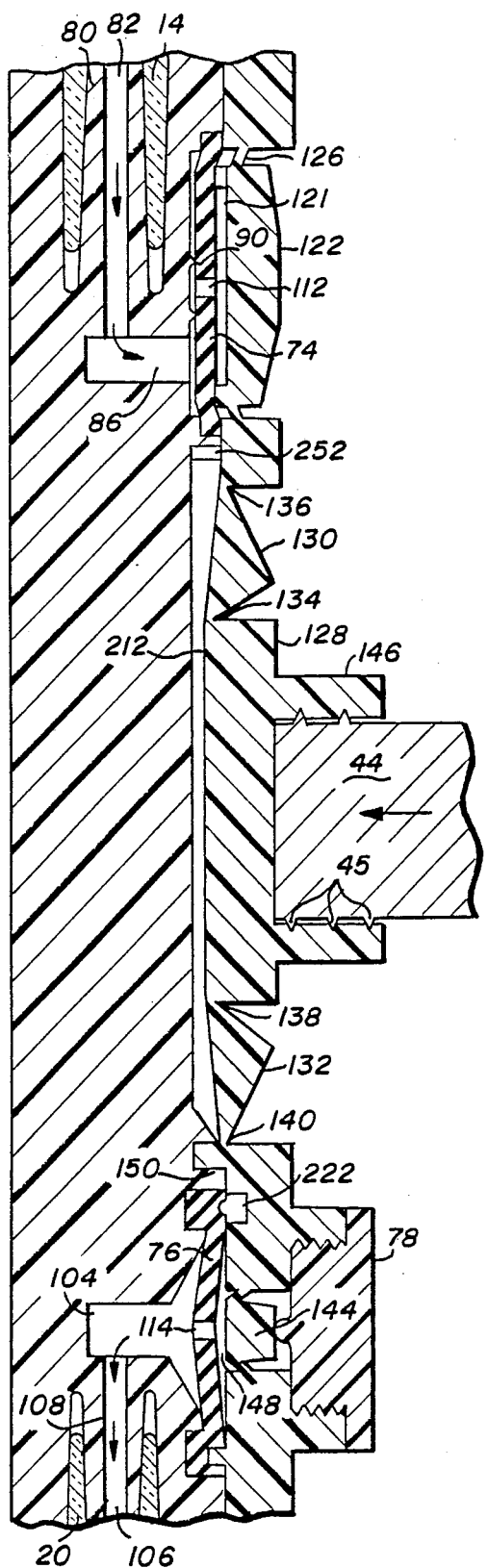
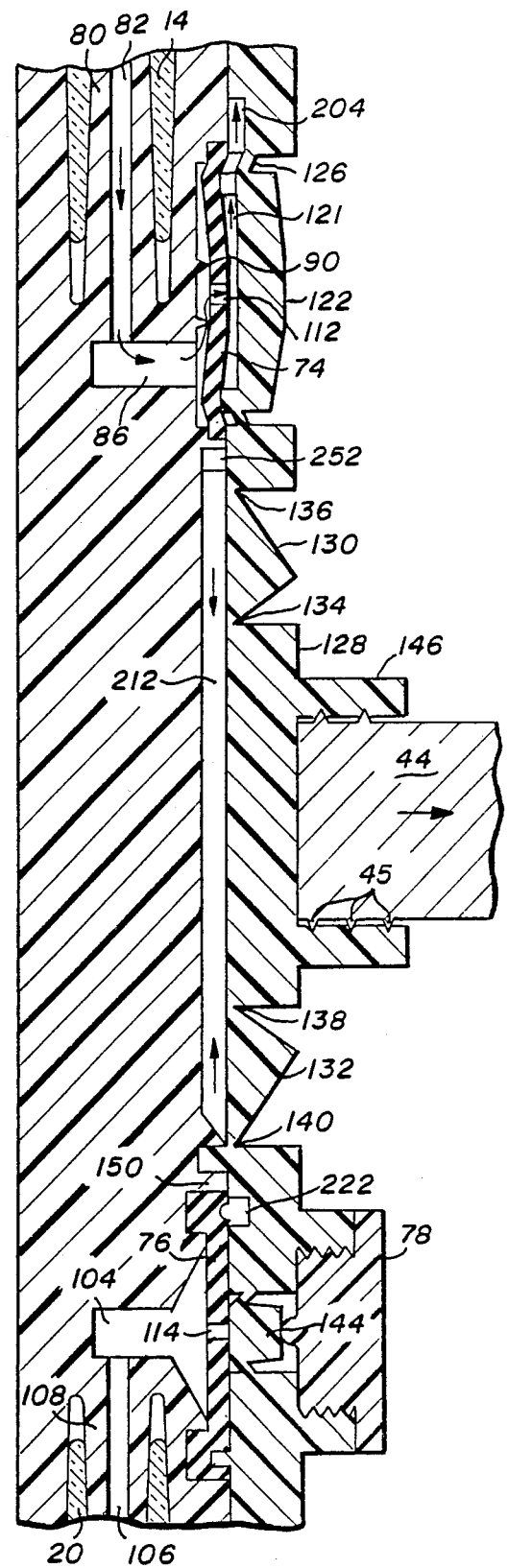
Fig_12
Fig_13

PARENTERAL SOLUTION PUMP ASSEMBLY

RELATIONSHIP TO COPENDING APPLICATION

This application is a division of application Ser. No. 902,616, filed Sept. 2, 1986, now U.S. Pat. No. 4,768,547, which is a continuation-in-part of application Ser. No. 799,235, filed Nov. 18, 1985, now U.S. Pat. No. 4,759,264.

FIELD OF THE INVENTION

This invention relates to improvements in fluid delivery systems, and in particular to parenteral solution or intravenous pumps which have a disposable pumping cassette.

BACKGROUND OF THE INVENTION

Pumping systems for the delivery of fluids intravenously or intra arterially are well known in the prior art and are in widespread daily use in hospitals throughout the world. These systems are commonly used for the intravenous or intra arterial delivery of such fluids as glucose solutions and blood plasma, and for the delivery of drugs, all at controlled delivery rates based on the patient's need, and in the case of drugs, the drug concentration being delivered.

The oldest and most commonly used fluid delivery system relies on a gravity feed. Pumping systems offer advantages of mobility and positive control of flow rates by pump motor control. The prior art pumps include both peristaltic pumps and positive displacement pumps. Both have the disadvantage of high cost and high operating expense. Portable units consume large amounts of power and require large, heavy battery packs, and the disposable pumping chambers are complex and expensive.

DESCRIPTION OF THE PRIOR ART

Pumps which squeeze or apply a positive fluid displacement member against a tube or pumping chamber segment and control fluid flow to and from the pumping chamber with further positively controlled tube pinching members including peristaltic pumps and similar systems are described in U.S. Pat. Nos. 4,199,307, 4,273,121 4,290,346, and 4,515,589, for example. A combination of a peristaltic pump and a back pressure monitor is described in U.S. Pat. No. 4,460,355.

Syringe pumps are described in U.S. Pat. No. 3,739,943 using a disposable hypodermic syringe as the pumping chamber and with a back pressure monitor. A syringe pump is also disclosed in U.S. Pat. No. 4,515,591.

A piston pump with a radially segmented spring element is described in U.S. Pat. No. 4,276,004. Piston pumps with the piston or equivalent displacement member covered with an elastic rubber barrier to isolate the pump chamber from the drive members are described in U.S. Pat. Nos. 4,140,118, 4,336,800, 4,453,931, 4,453,932, 4,457,753, and 4,519,732. Most piston pumps have inlet and outlet check valves. One or both of the inlet and outlet check valves in U.S. Pat. Nos. 4,126,132 and 4,468,222 are open during a fluid priming step prior to loading the pumping cassette into the operating housing, and are automatically activated into an operational position by the insertion of the cassette into the housing. In U.S. Pat. No. 4,468,222, the disposable cassette comprises an elastic diaphragm defining one wall of the pumping chamber and inlet and outlet valve members of a one piece molded construction.

Diaphragm pumps usually have resilient diaphragm members which are connected to a drive member, and are usually combined with inlet and outlet check valves as described in U.S. Pat. Nos. 2,812,716 and 2,954,738. These pumps lack the accuracy required for parenteral solution delivery because the diaphragm flexure during the positive pressure and negative pressure cycles alter the volume of the pumping chamber in a non-linear function which cannot be adequately compensated with programming. Diaphragm pumps comprising concentric cylindrical segments isolated from the pumping chamber with a rubber diaphragm are described in U.S. Pat. Nos. 1,923,970 and 3,200,757. However, these high friction diaphragms are unsuitable for use in parenteral solution delivery systems, and do not have the advantages of the unitary segmented diaphragm of the pump of this invention.

Segmented diaphragms have also been used in valve structures such as are described in U.S. Pat. Nos. 1,034,323, 1,229,860, 4,078,580, 4,208,031 and 4,231,287. A segmented diaphragm has been used in a camera lens positioning system in U.S. Pat. No. 3,677,161 and in a pressure controller in U.S. Pat. No. 4,364,386.

SUMMARY AND OBJECTS OF THE INVENTION

A disposable diaphragm pump cassette comprises a flexible diaphragm member comprising hinged, rigid plates hingingly mounted on an inflexible plate and opposed to a pumping chamber surface to form a pumping chamber. The pump includes check valve means comprising movable circular plates integrally connected with the inflexible plate by flexible, extendable webs. The flexible diaphragm member can comprise at least three inflexible diaphragm plates with edges in a common plane, each diaphragm plate having at least two straight diaphragm plate hinge edges. Each diaphragm plate hinge edge is adjacent to and aligned with a second diaphragm plate hinge edge of an adjacent diaphragm plate. The adjacent edges of each diaphragm plate hinge edge and second diaphragm plate hinge edge are attached together by a flexible hinge strip.

A preferred inlet check valve comprises an inlet check valve plate, a valve seat means opposing the check valve plate, and a flexible diaphragm disk with a central flow passageway between the inlet check valve plate and the valve seat means. In this embodiment, the flexible inlet diaphragm disk has an inlet side facing the valve seat and communicating with a fluid inlet, and an outlet side facing the inlet check valve plate and communicating with the pumping chamber. The inlet check valve plate is a check valve activation member which by pressing the flexible inlet diaphragm disk against the valve seat means, activates the inlet check valve.

A preferred outlet check valve comprises an outlet check valve plate including a valve seat means, an outlet check valve chamber opposing the valve seat means, and a flexible outlet diaphragm disk with a central flow passageway between the outlet check valve plate and the outlet check valve chamber. In this embodiment, the flexible outlet diaphragm disk has an inlet face facing the valve seat means and communicating with the pumping chamber and an outlet face facing the outlet check valve chamber and communicating with a fluid outlet. The outlet check valve plate is a check valve activation member which by pressing the valve seat means against the flexible outlet diaphragm disk, activates the outlet check valve.

One object of this invention is to provide a parenteral solution pump with a low cost disposable cassette comprising the pumping chamber and valve structures, made of few inexpensive, easily molded parts, which can be assembled and joined with a minimum of labor and a low defect rate.

Another object of this invention is the provision of a high accuracy pump which requires a small amount of energy for operation, and which is easy to prime, install and operate.

These and other objects of this invention will be readily apparent in the description of the invention presented hereinafter.

BRIEF DESCRIPTION OF THE DRAWINGS

FIG. 1 is a schematic representation of a parenteral pump delivery system.

FIG. 2 is a partial cross-sectional representation of the pump of this invention positioned in engagement with the drive system and motor housing.

FIG. 3 is an exploded cross-sectional representation of one embodiment of the disposable cassette elements prior to assembly.

FIG. 4 is a fragmentary detailed cross-sectional view of the swage closure elements of the front and back plates shown in FIG. 3 during assembly.

FIG. 5 is a fragmentary detailed cross-sectional view of the swage closure of the front and back plates shown in FIG. 3 after assembly.

FIG. 6 is a back view of the back plate shown in FIG. 3.

FIG. 7 is a front view of the back plate shown in FIG. 3.

FIG. 8 is a cross-sectional view of the back plate shown in FIG. 7, taken along the line 8—8.

FIG. 9 is a back view of the front closure plate shown in FIG. 3.

FIG. 10 is a partial cross-sectional view of the cassette assembly showing the pump diaphragm and inactive check valves during priming.

FIG. 11 is a partial cross-sectional view of the cassette assembly of FIG. 10 showing the check valves after activation.

FIG. 12 is a partial cross-sectional view of the installed cassette assembly of FIG. 10 during the output phase of the pumping cycle.

FIG. 13 is a partial cross-sectional view of the installed cassette assembly of FIG. 10 during the filling phase of the pumping cycle.

FIG. 14 is a partial, fragmented view of the disposable cassette of this invention mounted on the motor housing.

DETAILED DESCRIPTION OF THE INVENTION

The parenteral solution delivery pump of this invention has a low cast, disposable cassette comprising a few molded parts which can be easily assembled. It provides economy in construction and operation. The pump housing and cassette, including power source and controller, are portable and light in weight.

FIG. 1 is a schematic representation of a parenteral pump delivery system according to this invention. The fluid bag or bottle 2 is suspended on the standard clinical support pole 4. The fluid administration set includes the standard drip chamber 6 and Y-junction 8. The drip chamber can be combined with an optional drop monitor 12. The flexible tubing 14 extends to and connects with the pump cassette 16 shown mounted in the pump and controller housing 18. The outlet tubing 20 connects with the pump cassette 16 and leads to the patient being treated.

FIG. 2 is a partial cross-sectional representation of the pump 16 of this invention positioned in engagement with the motor and controller housing 18 and the drive system enclosed therein. The DC motor 24 has a drive shaft 26 supported by bearing 28, the distal end of the drive shaft 26 being connected to a drive wheel 30. The drive wheel 30 has a cam groove 32 in the back face thereof engaged by the cam follower 34 attached to the movable end 36 of the drive beam 38. The opposite end 40 of the drive beam 38 is mounted for pivotal movement around pin 42. The male drive connector 44 with barbs or self-threading threads 45 is attached to a central portion of the drive beam 38, and engages a female receptor 46 integral with the central diaphragm plate on the back plate of the pump cassette 16. The flexible plate diaphragm is described in our copending application Ser. No. 799,235 filed Nov. 18, 1985, the entire contents of which are hereby incorporated by reference in its entirety. The flexible plate diaphragm will be shown in greater detail hereinafter.

The distance of the cam groove 32 from the central axis of the drive shaft 26 varies as the drive shaft rotates, translating the rotary motion of the drive shaft to a reciprocating displacement of the cam follower 34 and cassette drive connector 44. The drive connector 44 thus imparts a reciprocating motion to the diaphragm plate of which the female drive connector 46 is a part. An annular flexible splash shield 48 is secured to the male drive connector and the surrounding edges of the housing 18 to prevent liquid contaminants from reaching the interior of the housing 18.

Inlet tubing 14 from the liquid source 2 (FIG. 1) is secured to a tubing connector inlet 50 of the cassette 16. Outlet tubing 20 extending to the patient is secured to a tubing connector outlet 52 of the cassette.

The cassette 16 is secured to the housing 18 by tabs or ears 54 and 56 extending from the cassette 16 into corresponding grooves defined by retention projections 60 and 62 extending from the front of the housing.

FIG. 3 is an exploded cross-sectional representation of one embodiment of the five disposable cassette elements prior to assembly.

The disposable pump cassette 16 comprises a front plate 70, back plate 72, resilient inlet check valve washer 74, resilient outlet check valve washer 76 and outlet check valve engaging knob 78. The front plate 70 has an inlet tube connector 50 consisting of a nipple extension 80 with an inlet fluid passageway 82 for entering and expanding the tubing 14 (FIG. 1), and a surrounding annular recess 84 for receiving the tubing wall as the tubing is slipped over the nipple 80. The inlet passageway 82 communicates with the inlet check valve inlet 86 and annular inlet check valve cavity 88. The inlet check valve cavity 88 surrounds the stationary valve seat element 90. A circular inlet check valve washer receptor is defined by annular rim 92 for supporting the edges of the check valve washer 74.

Swage joint groove 94 and swage projection 96 extend completely around the back face edge of the front plate 70. Pumping cavity 98 is positioned on the back face of the front plate 70 between the inlet check valve elements and the outlet check valve elements.

The outlet check valve elements of the front plate include the outlet check valve washer receptor defined by the annular groove 100 which surrounds the conical outlet check valve cavity 102. The outlet check valve outlet 104 communicates with the cavity 102 and the outlet flow passageway 106 in the outlet tubing nipple extension 108 of the outlet tubing connector 52. The nipple 108 is surround by an annular tubing receptor 110 which receives the outlet tubing when it is slipped over the end of the nipple 108.

The inlet check valve washer 74 is a resilient, elastic material in the form of a disk with a central flow passageway 112. The outlet check valve washer 76 is a resilient, elastic material in the form of a disk with a central flow passageway 114.

The back check valve plate 72 is also of unitary construction and includes the check valve activation elements, segmented pump diaphragm, and pump drive connector element. Whereas the front plate 70 is made of rigid plastic, the back plate is made of a plastic such as polyethylene which is essential rigid in thickened portions and flexible and extendable in thinned connecting portions.

The thickened, inflexible back plate 120 surrounds and is connected to the thickened, inflexible inlet check valve activation disk 122 by the flexible, extendable annular connecting web 124. The front face of the disk 122 has an annular raised ridge 126. The pump diaphragm comprises an inflexible central plate 128 integral with the female pump drive receptor 46, surrounded by the inflexible back plate 120 and connected thereto by rigid, hinged pump segments 130 and 132. Pump segment 130 is connected to the central plate 128 by thinned, flexible hinge portions 134 and to the back plate 129 by the thinned, flexible hinge portion 136. Pump segment 132 is connected to the central plate 128 by thinned, flexible hinge portion 138 and to the back plate 120 by the thinned, flexible hinge portion 140.

Outlet check valve elements of the back plate 72 comprise a threaded outlet check valve activation knob receptor 142 which is integral with the back plate 120 and extending outward rearwardly therefrom. The thickened, inflexible outlet check valve activation disk 144 is connected to the bottom edge of the knob receptor 142 by a thinned, flexible, extendable annular web 146. The circular outlet check valve cavity is defined by circular recess 148 in the front, central face of the disk 144. Annular raised ridge 150 extending from the front face of the outlet check valve portion of the plate 120 secures the outlet check valve disk 76 in place when the front and back pieces are joined. Swage joint ridge element 152 extends from the front face of the periphery of the back plate 72.

Outlet check valve activation knob 78 has a grip flange portion 160, a threaded cylindrical portion 162 for engaging the threaded receptor 142, and an axially concentric projection 164 for engaging the opposing surface of the outlet check valve disk 144 when advanced thereagainst.

FIG. 4 is a fragmentary detailed cross-sectional view of the swage closure elements of the front and back plates shown in FIG. 3 during assembly, and FIG. 5 is a view of the swage closure of the front and back plates shown in FIG. 3 after assembly. The swage closure groove 94 of the front plate 70 is defined by a wall surface 168 in the back side of the front plate and a ridge 170 having a wall surface 172. The opposite side 174 of the ridge 170 slopes to form a knife-edge projection extending from the front plate which will be swaged to form a secure closure. The bottom of the swage closure groove has sharp edged sealing ridges 176. Sharp knife-edge ridges 176 extend toward the opposing face 178 of the swage closure ridge 152 of the back plate 72. Swage joint ridge element 152 has a forward face 178 opposing the sealing ridges 176 and sloped sidewalls 180 and 182 which engage the corresponding sloped sidewalls 168 and 172 of the swage closure groove in tight compression to form a liquid-tight seal. Swage closure abutment surface 184 is parallel to surface 178.

In FIG. 5, the completed swage closure joint is shown. The knife-edged ridges formed of rigid plastic of the front plate are forced into the opposing surface 178 of the closure ridge made of the softer plastic of the back plate under high pressure to form a second liquid tight seal. The leading edge of the ridge 170 is swaged over the abutment surface 184 under high pressure to form a secure engagement which will rigidly retain the front and back plates in permanent engagement. The swage groove and ridge extend around the entire periphery of the cassette, and thus form a liquid tight dual seal around the edge of the cassette. The swage closure and seals are required when the materials from which the front and back plates are formed are incompatible and cannot be securely joined by welding, solvent bonding, gluing or other standard procedures. Optimally, the back plate is made of a material which is relatively rigid when thick, and yieldable and flexible when in a thin cross-section. Examples of such materials are polyolefins such as low and high density polyethylene, optimum materials for the back plate. In contrast, the front plate requires a high rigidity and is preferably formed with ABS polymer or the like which cannot be securely bonded to polyethylene. The dual sealed swage closure of this invention joins such two incompatible plastics together to form a secure unitary construction which will not leak liquid from the inner chamber.

FIG. 6 is a back view of the back plate shown in FIG. 3, FIG. 7 is a front view of the back plate, and FIG. 8 is a cross-sectional view of the back plate shown in FIG. 7, taken along the line 8—8. In FIG. 6 the overall configuration of the check valves and diaphragm shown in cross-section in FIG. 3 can be seen. The rigid hexagonal diaphragm plate 128, on which the drive receptor 46 is supported, is joined to the surrounding rigid back plate 72 by six rigid trapezoidal plates, the optimum configuration for a pump of this size. Each trapezoidal plate is joined to the back plate by a thinned, flexible, yieldable hinge such as 136 and 140, and is joined to the hexagonal diaphragm plate 128 by a thinned, flexible, yieldable hinge such as 134 and 138. The adjacent edges of adjacent trapezoidal plates are joined by thinned, flexible, yieldable hinges such as 131 and 133, for example. This pattern is repeated with each trapezoidal plate.

The preferred, flexible diaphragm member has at least three inflexible diaphragm plates with edges in a common plane, each diaphragm plate having at least two straight diaphragm plate hinge edges. Each diaphragm plate hinge edge is adjacent to and aligned with a second diaphragm plate hinge edge of an adjacent diaphragm plate. The adjacent edges of each diaphragm plate hinge edge and second diaphragm plate hinge edge are attached together by a flexible hinge strip. Optimally, when the first array of plates comprises at least three identical plates having identical edges, the respective identical edges thereof are positioned equally distant from the axial center of symmetry. Additionally, the flexible member can include a central plate as shown in FIG. 6, the axial center of the center plate being at the axial center of symmetry. The center plate optimally has straight plate edges having the same length, and the plates include an array of plates hingingly connected to the straight sides of the center plate. Each plate in the array of plates then has a straight center plate hinge edge positioned adjacent to and aligned with a center plate edge and hingingly connected at the center plate edge by a flexible hinge strip.

In the embodiment illustrated in the drawings, a total of six plates are assembled in a symmetrical array around the axial center. It will be readily apparent that the number of plates can be selected as described, a minimum of three plates being required for operation in the intended manner. The flexible hinge elements are distorted by both flexure and stretching during the movement of the diaphragm element, and as the number of segments are reduced, greater energy is expanded to effect flexure. Stretch distortion of the hinge increases toward the center of the diaphragm, and this distortion is increased by reducing the number of plates. Increasing the number of segments increases the flexible hinge area and reduces the stretching required for diaphragm movement, both reducing energy requirements. Increasing the hinge width and reducing the thickness of the hinge also increases hinge flexibility and elasticity, further reducing energy requirements. However, increasing the number of plates, increasing the relative hinge area and reducing the hinge thickness increases non-linear pumping errors.

An important achievement of the flexible plate diaphragm is the reduction of pumping volume variations which are a function of liquid pressure. Liquid pressure rising in the pumping chamber during a positive pumping stroke and falling during the filling stroke tends to stretch the diaphragm, increasing or decreasing the volume of the pumping chamber, and introducing a non-linear variable in the liquid volume output or input per stroke. The volume displaced during a positive stroke is thus less than would be calculated by simple displacement, and the volume filled during a filling stroke is less than would be calculated by a simple displacement calculation. Because the degree of distortion is a function of the varying pumping chamber pressures, which is in turn, a function of the pumping rate and outlet valve and line back-pressure, this type of distortion cannot be adequately compensated by microcomputer control adjustments and seriously impairs pumping accuracy.

This effect is very pronounced with the flexible diaphragm pumps known prior to this invention. Piston pumps, while avoiding this problem, use more power and require a more complex construction to prevent leakage from the pumping chamber around the piston.

With the plate diaphragm construction of this invention, however, the increased pressure in the pumping chamber does not significantly flex the plate elements, and a more linear relationship between displacement and delivered volume is achieved. With the hinged plate diaphragm of this invention, diaphragm flexure is resisted by the relatively inflexible plates. Only the hinge areas will flex. Thus, the areas subject to flexure are minimized, consistent with the designed power and pressure restraints of a portable battery operated unit, for example. The diaphragm of FIG. 1, having a central plate and six equal segments, represents a studied compromise of these factors, and is believed to represent a preferred configuration for use with the pump configuration for parenteral solution delivery shown in the drawings.

The plate bearing the flexible plate components and the individual plate element of the diaphragm are preferably relatively rigid to achieve maximum accuracy. This can be achieved by bonding rigid plate elements to a flexible sheet. For example, a relatively rigid polymer can be bonded to a flexible, elastic polymer, combining the rigidity and flexibility desired. In a preferred embodiment of this invention, elements of the front plate bearing the hinged plate diaphragm are formed from a single, homogeneous sheet of plastic. Rigidity is achieved by thickness and flexibility by thinness. Polyolefin plastics such as polyethylene can be used for this construction, for example. In this embodiment, the rigid plates and the flexible hinges are integral parts of a single unit. Corresponding check valve elements can be similarly formed in same the sheet of plastic. The back plate can be made of a suitable rigid plastic such as ABS polymer.

Referring to FIG. 7 and FIG. 8, the front surface of the back plate 72 is shown. Within the swage ridge 152 extending around the periphery of the back plate are positioned the check valves 122 and 144 and the grooves and ridges which together with the corresponding grooves and ridges of the front plate form the valve and pumping cavities and fluid flow passageways in the cassette. The inlet check valve face 122 is surrounded by circular ridge 200 which presses the inlet check valve disk 74 (FIG. 3) against the edge of the inlet check valve disk receptor 92 of the front plate. This is surrounded by a circular liquid flow channel groove 202 leading to inlet channels 204 and 206. The inlet channel 206 leads toward the pumping chamber defined by the ridges 208 and 210 surrounding the inner surface 212 of the pump diaphragm. Groove 214 having an inlet end 216 constitutes an optional air-in-line fluid flow passageway, directing the fluid along a narrow passageway of precise dimensions and returning the fluid to exit at 218. If this type of air-in-line detector is to be omitted, this passageway is omitted entirely. The fluid is then directed by a passageway in the front plate to the inlet 220 of the outlet check valve passageway 222 leading to the outlet check valve chamber 144. The ridge 224 surrounding the check valve chamber 144 presses the outlet check valve disk 76 (FIG. 3) against the edge of the outlet check valve receptor 100 of the front plate.

FIG. 9 is a back view of the front closure plate shown in FIG. 3. The flow passageways in the cassette are formed by a pattern of aligned grooves or channels in the back side of the front closure plate shown in FIG. 9 and the corresponding, engaging front surface of the back plate shown in FIG. 7. The grooves of channels, together with the flat opposing surface of the opposite plate, define enclosed passageways, and references to features shown in FIG. 7 and in FIG. 9 are made in the following description.

The four tabs or mounting flanges 54 and 56 are positioned with one at each corner of the cassette. The swage groove 94 and swage ridge 96 extend around the entire periphery of the front plate. The circular configuration of the inlet check valve structure with inlet passageway 86 and the concentric valve seat 90 and check valve disk receptor 92 are positioned at the upper portion of the front plate positioned to oppose the respective elements of the back plate. The valve seat 90 comprises a raised circular ridge for abutting the inlet check valve washer or diaphragm 74 The outlet check valve elements are concentric; the outlet passageway 104, valve cavity defining cone 102 and the outlet check valve disk receptor are formed in the back surface of the front plate.

The perimeter of the hexagonal diaphragm pump chamber 230 is defined by six sloped edge surfaces 232, 234, 236, 238, 240 and 242. Fluid is further confined within the pump chamber by engaging ridges and grooves on five sides of the pump chamber, parallel to the sloped edge surfaces, and positioned adjacent to the sloped surfaces exterior to the pump chamber. Fluid retention groove 244 is positioned to engage the corresponding fluid retention ridge 210 (FIG. 7). Fluid retention groove 246 extending around four sides of the hexagon is positioned to engage the corresponding fluid retention ridge 208. The close proximity of the pressure swage seal of the edge 248 closely adjacent to and bordering the sixth side 240 of the sloped edge surface provides an effective fluid retention barrier on the sixth side of the pump chamber hexagon.

The pump chamber inlet groove 250 is positioned at the inlet end of the cassette to communicate with the end 207 of the inlet groove 206, for direction of fluid flow from the inlet check valve chamber directly to the pumping chamber. The end of the pump outlet groove 252 is positioned at the inlet end of the cassette to communciate with the inlet end 216 of the optional air-in-line detection passageway 214 (FIG. 7). The fluid flow passageway 254 directs fluid flow to the vicinity of the outlet check valve at the outlet end of the cassette. The inlet end 256 of the fluid outflow passageway 254 communicates with the outlet end 218 of the optional air-in-line detector passageway. The outlet end 258 of the fluid outflow passageway 254 communicates with the inlet end 220 of the outlet check valve inlet passageway 222 (FIG. 7). If the groove 216–218 is omitted, the groove ends 252 and 256 communicate directly, and liquid flows directly from the outlet 252 to the inlet 256 of the fluid outflow passageway 254.

FIG. 10 is a partial cross-sectional view of the cassette assembly showing the pump diaphragm and inactive check valves during priming, and FIG. 11 is a view of the cassette assembly showing the check valves after activation. Initially, the knob 78 is rotated to press the element 144 against the diaphragm disk 76 to activate the check valve, the position shown in FIG. 11. This closes the outlet valve, and in this position, the pump cassette can perform the functions of a traditional roller clamp, preventing fluid flow through the system until desired. After connecting the inlet tubing 14 to the inlet tubing nipple 80 and to the liquid source, and after connecting the outlet tubing 20 to the outlet tubing nipple, the outlet check valve is deactivated (opened) by rotating the knob 78 to the position shown in FIG. 10. Liquid then flows from the source 2 through the inlet tubing 14, inlet passageway 82 and into the inlet check valve inlet 86. The inlet check valve washer or diaphragm 74 is spaced from the seat 90 of the inlet check valve, and fluid passes between the ridge 90 and the opposing surface of the inlet check valve diaphragm and through the central opening 112 of the check valve diaphragm. The fluid then passes across the face of the inlet check valve actuator and to the outlet passageway 204. The fluid is then directed to the diaphragm pump chamber, displacing air in the pump chamber until it is filled with fluid. The fluid then continues to pass through the optional air-in-line detector loop 214 (FIG. 7) and passageway 254 until it reaches the outlet check valve chamber, entering through passageway 222. Since the outlet check valve diaphragm opening 114 is unobstructed, fluid is free to pass through the opening 114, into the outlet check valve chamber 104, through the outlet passageway 106 and to the outlet tubing 20. Air is thus displaced from the pumping unit, and it is primed for operation.

The knob 78 is then turned to activate (depress) the outlet check valve, moving the central disk 144 into contact with the outlet check valve diaphragm and blocking the central opening 114 in the outlet check valve diaphragm 76. The thinned continuous web portion 146 stretches without breaking, permitting movement of the central disk 144 without detachment from the back plate or loss of integrity of outlet check valve. The final position is shown in FIG. 11. The primed, set pump cassette of this invention is then mounted on the motor drive housing in the position shown in FIG. 2, the self-threading motor drive member 44 securely mounted in the drive receptor 146.

The pumping cassette connected to the motor drive is shown in FIG. 11, with the exception that the motor drive housing is not shown. In being mounted in the motor drive housing, the inlet check valve member 122 is depressed by a protruding surface of the housing. The central disk 122 is pressed toward the inlet check valve diaphragm 74, the circular ridge 200 pressing the diaphragm 74 inward and against the raised circular ridge of the valve seat 90. Thus the inlet check valve is activated by the operation of pressing the pumping cassette against a raised portion of the motor drive housing.

It will be readily apparent to a person skilled in the art that the outlet check valve can also be constructed to be activated by a portion of the motor drive housing rather than a separate knob 78, or that the inlet check valve can be constructed to be separately activated by a control knob rather than the motor housing surface, and both of these alternative embodiments are included within this invention. However, the embodiment shown in FIGS. 10 and 11 is the preferred embodiment. After pumping is terminated, the pumping cassette can be disconnected from the motor drive and removed from the motor drive housing. The inlet check valve will be inactivated to the open position upon return of the inlet check valve elements to the initial priming position shown in FIG. 10. The knob 78 can be rotated to a position which establishes the desired gravity flow rate, assuming the fluid source is positioned at a higher elevation such as shown in FIG. 1.

FIG. 12 is a partial cross-sectional view of the installed cassette assembly of FIG. 10 during the output phase of the pumping cycle, and FIG. 13 shows the installed cassette assembly during the filling phase of the pumping cycle. During the output phase, the motor drive element 44 advances toward the pumping cassette, moving the face 212 of the central diaphragm segment 128 toward the opposing face of the pump chamber cavity, thus reducing the volume of the pumping chamber. This movement is permitted by the flexure (with some stretching) of the hinge segments 134, 136, 138 and 140 and the corresponding movement of the rigid plate segments 130 and 132. The combination of the rigid plate segments and small area of the hinges provides and prevents any significant distortion of the pumping chamber volume due to flexure of the pumping surfaces in the manner of resilient pump diaphragms. The pump of this invention thus combines the unique features of a diaphragm pump with the precision of a piston pump. With the pump configuration of this invention, an output volume which is a function of the pumping displacement is achieved, permitting the control precision of a piston pump with the simple construction and energy efficiency of a diaphragm pump.

The fluid expressed from the pumping chamber is expelled through the outlet passageway 252 and eventually to the outlet check valve. The fluid pressure between the element 144 and the outlet check valve diaphragm 76 displaces the diaphragm surface from the surface of the element 144, exposing the diaphragm passageway 114. Liquid passes through opening 114 and the outlet passageway 106 to tubing 20. Reverse flow of liquid to the source is prevented by the construction of the inlet check valve. The volume 121 defined by the surface of the actuator 122, the ridge 200 and the inlet check valve diaphragm 74 is in direct communication with the pumping chamber, and the increased pressure of the output phase of the pump presses the diaphragm 74 securely against the seat 90, preventing fluid escape to the inlet passageway.

The reverse flow of the filling phase of the pump is shown in FIG. 13. Reverse motion of the pump element 44 pulls the central rigid diaphragm segment 128 away from the opposing surface of the front plate, increasing the volume of the pumping chamber. The rigid, hinged plates 130 and 132 follow, the plate structure bending about the hinges 134, 136, 138 and 140. The rigid plate construction again achieves a volume change which is a direct function of the displacement of the actuator 44, achieving a precise filling volume. The volume is not affected significantly by the difference in pump chamber pressure and atmospheric pressure.

The pressure in the pumping chamber and chamber 121 during the filling phase falls below the relative pressure in the inlet conduit 82 and inlet check valve inlet 86. The inlet fluid pressure displaces the face of the inlet check valve diaphragm 74 away from the valve seat 90, permitting liquid flow through the inlet check valve to the passageway 204 and to the pumping chamber. The pressure is the outlet flow passageway 106 and outlet check valve chamber 104 also exceeds the pressure in the pumping chamber during the filling phase, pressing the outlet check valve diaphragm 76 firmly against the surface of the outlet check valve element 144. Reverse flow of liquid from the outlet conduit 20 during the filling phase is thus prevented.

The outlet check valve assembly provides an additional safety feature. If the cassette 16 becomes dislodged from the housing 18, the outlet check valve actuator 144 remains in the forward position, pressing against the disk 76 and preventing any further fluid flow to the patient.

FIG. 14 is a partial, fragmented view of the disposable cassette of this invention mounted on the motor housing. The mounting tabs or ears 54 and 56 on the front plate (FIG. 9) are engaged with mounting groove 250 (shown as dotted lines) defined by the upper mounting flanges 60 and 61 and mounting groove 252 by clockwise rotation of the cassette 16. The rotation is terminated by the abutment of the tabs with the ends of the groove, 254 and 256. The drive element 44 is fixed against rotation about its axis. Rotation of the cassette to engage the tabs 54 and 56 with the mounting flanges 60 and 61 threads the receptor 46 onto the barbs or self-threading screw threads 45 on the surface of the drive element 44.

We claim:

1. A diaphragm pump cassette for use with a pumping mechanism comprising a pumping chamber, and a check valve means communicating with the pumping chamber, said check valve means including a first check valve and a second check valve, each check valve including a valve seat, a flexible valve diaphragm, and moveable valve seating means for locating said diaphragm on said valve seat, said valve diaphragms being unseated with respect to said valve seat prior to mounting said pump cassette on said pumping mechanism whereby fluid may flow freely through said check valve means, further including a cassette back plate, wherein said valve seating means is a check valve plate attached to the back plate by a flexible hinge means.

2. The diaphragm pump cassette of claim 1 wherein said valve seating means of said first check valve includes means, independent of said pumping mechanism, for manually opening and closing said first check valve.

3. The diaphragm pump cassette of claim 5 wherein said cassette is operable with said pumping mechanism only when said diaphragm of said first check valve is seated on its valve seat, said first and second check valves being capable of opening and closing in response to pressure changes developed in said pumping chamber when said diaphragms are seated on said valve seats.

4. The diaphragm pump cassette of claim 1 wherein the closing of said first check valve by said manually opening and closing means cause said valve seating means of said first check valve to seat the diaphragm of the first check valve on its valve seat; and wherein said valve seating means of said second check valve automatically seats the diaphragm of said second check valve on its valve seat when said cassette is mounted on said pumping mechanism.

5. The diaphragm pump cassette of claim 1 wherein said means for manually opening and closing said first check valve includes an adjustment means threadingly engaging the back plate and having a surface opposing the check valve plate for pressing the check valve plate toward the diaphragm.

6. The diaphragm pump cassette of claim 1 wherein the second check valve is an inlet check valve comprising an inlet check valve plate, a valve seat opposing the check valve plate, and a flexible diaphragm disk with a central flow passageway between the inlet check valve plate and the valve seat.

7. The diaphragm pump cassette of claim 6 wherein the flexible inlet diaphragm disk has an inlet side facing the valve seat and communicating with a fluid inlet, and an outlet side facing the inlet check valve plate and communicating with the pumping chamber, the inlet check valve plate being a check valve activation member which by pressing the flexible inlet diaphragm disk against the valve seat closer the inlet check valve.

8. The diaphragm pump cassette of claim 1 wherein said first check valve is an outlet check valve comprising an outlet check valve plate including a valve seat, an outlet check valve chamber opposing the valve seat, and a flexible outlet diaphragm disk with a central flow passageway between the outlet check valve plate and the outlet check valve chamber.

9. The diaphragm pump cassette of claim 8 wherein the flexible outlet diaphragm disk has an inlet face facing the valve seat and communicating with the pumping chamber and an outlet face facing the outlet check valve chamber and communicating with a fluid outlet, the outlet check valve plate being a check valve activation member which by pressing the valve seat against the flexible outlet diaphragm disk, closes the outlet check valve.

* * * * *